(12) United States Patent
Thein et al.

(10) Patent No.: US 10,441,197 B2
(45) Date of Patent: Oct. 15, 2019

(54) DEVICE AND METHOD FOR CLASSIFYING THE ACTIVITY AND/OR COUNTING STEPS OF A USER

(71) Applicants: Khine Cho Cho Thein, Singapore (SG); Kittipong Kasamsook, Singapore (SG); Aye Aung, Singapore (SG); NITTO DENKO CORPORATION, Osaka (JP)

(72) Inventors: Khine Cho Cho Thein, Singapore (SG); Kittipong Kasamsook, Singapore (SG); Aye Aung, Singapore (SG)

(73) Assignee: NITTO DENKO CORPORATION, Osaka (JP)

( * ) Notice: Subject to any disclaimer, the term of this patent is extended or adjusted under 35 U.S.C. 154(b) by 269 days.

(21) Appl. No.: 15/315,090

(22) PCT Filed: May 30, 2014

(86) PCT No.: PCT/SG2014/000248
§ 371 (c)(1),
(2) Date: Nov. 30, 2016

(87) PCT Pub. No.: WO2015/183193
PCT Pub. Date: Mar. 12, 2015

(65) Prior Publication Data
US 2017/0188897 A1    Jul. 6, 2017

(51) Int. Cl.
*A61B 5/00* (2006.01)
*A61B 5/11* (2006.01)
(Continued)

(52) U.S. Cl.
CPC ........... *A61B 5/1123* (2013.01); *A61B 5/1118* (2013.01); *A61B 5/7207* (2013.01);
(Continued)

(58) Field of Classification Search
CPC ..... A61B 5/1118; A61B 5/1123; A61B 5/112; A61B 5/7207; A61B 5/7221; A61B 2562/0219
See application file for complete search history.

(56) References Cited

U.S. PATENT DOCUMENTS 6,539,336 B1   3/2003   Vock
7,457,719 B1   11/2008  Kahn
(Continued)

FOREIGN PATENT DOCUMENTS

JP    2006122376 A    5/2006
JP    2010068968 A    4/2010
(Continued)

OTHER PUBLICATIONS

H. Ying et al., "Automatic Step Detection in the Accelerometer Signal," 4th International Workshop on Wearable and Implantable Body Sensor Networks (BSN 2007), IFMBE Proceedings 2007, vol. 13, pp. 80-85 (6 pages).
(Continued)

*Primary Examiner* — Max F Hindenburg
(74) *Attorney, Agent, or Firm* — Abelman, Frayne & Schwab

(57) ABSTRACT

Device and method for classifying the activity and/or counting steps of a user. A method for classifying the activity of a user can comprise measuring accelerometer data for a plurality of axes; identifying a most active one of the plurality of axes based on the accelerometer data; and classifying the activity of the user based on a signal amplitude of the accelerometer data for the most active axis and one or more threshold values.

10 Claims, 8 Drawing Sheets

(51) Int. Cl.
*G01C 22/00* (2006.01)
*G01P 15/00* (2006.01)

(52) U.S. Cl.
CPC .......... *A61B 5/7221* (2013.01); *G01C 22/006* (2013.01); *G01P 15/00* (2013.01); *A61B 5/11* (2013.01); *A61B 2562/0219* (2013.01)

(56) References Cited

U.S. PATENT DOCUMENTS

| | | | |
|---|---|---|---|
| 7,467,060 B2 | 12/2008 | Kulach | |
| 7,653,508 B1 | 1/2010 | Kahn | |
| 8,180,591 B2 * | 5/2012 | Yuen | A61B 5/0002 |
| | | | 702/160 |
| 8,909,330 B2 * | 12/2014 | McCombie | G16H 50/50 |
| | | | 600/513 |
| 9,398,867 B2 * | 7/2016 | Downs | A61B 5/1123 |
| 9,999,376 B2 * | 6/2018 | Chan | A61B 5/1116 |
| 2009/0319221 A1 | 12/2009 | Kahn | |
| 2012/0136573 A1 | 5/2012 | Janardhanan | |
| 2012/0291544 A1 | 11/2012 | Kawabe | |
| 2014/0129175 A1 | 5/2014 | Poduri et al. | |

FOREIGN PATENT DOCUMENTS

| | | |
|---|---|---|
| JP | 2011200390 A | 10/2011 |
| JP | 2012181110 A | 9/2012 |
| JP | 2014006090 A | 1/2014 |
| WO | 2008133921 A1 | 11/2008 |
| WO | 2010025467 A1 | 3/2010 |
| WO | 2010073044 A1 | 7/2010 |
| WO | 2011061412 A1 | 5/2011 |

OTHER PUBLICATIONS

Ryan Libby, "A simple method for reliable footstep detection on embedded sensor platforms," 2008 (16 pages).
Guillaume Thüer, "Step detection algorithms for accelerometers," Paper of the E-Lab Master Thesis, 2008 (8 pages).
N. Zhao, "Full-Featured Pedometer Design Realized with 3-Axis Digital Accelerometer," Analog Dialogue 44-06, Jun. 2010, 1-5 (5 pages).
M. Marschollek et al., "A performance comparison of accelerometry-based step detection algorithms on a large, nonlaboratory sample of healthy and mobility-impaired persons," 30th Annual International IEEE EMBS Conference Vancouver, British Columbia, Canada, Aug. 20-24, 2008, pp. 1319-1322 (4 pages).
A. Kuznietsov, "Inertial Measurement System for Performance Evaluation of Track and Field Sprinters," IEEE International Instrumentation and Measurement Technology Conference (I2MTC), 2012, pp. 1681-1686 (6 pages).
Office Action for counterpart Japanese Patent Application No. 2017-515663 (including English translation), dated Feb. 28, 2018 (21 pages).
Office Action for counterpart Japanese Patent Application No. 2017-515663 (including English translation), dated Oct. 24, 2018 (12 pages).

\* cited by examiner

Output before filtering a)

Output after derivative b)

DEVICE AND METHOD FOR CLASSIFYING THE ACTIVITY AND/OR COUNTING STEPS OF A USER

CLAIM FOR PRIORITY

This application claims priority to PCT/SG2014/000248, filed 30 May 2014.

FIELD OF INVENTION

The present invention relates broadly to device and method for classifying the activity and/or counting steps of a user.

BACKGROUND

In recent years, people are becoming more health conscious and have taken up running and walking as a convenient and effective way to exercise. There is also an increased interest in self-tracking of daily activities through wearable sensors. Hence there is need for a step counting device that can accurately record a wearer's gait status as well as the number of steps taken.

Conventional step counting devices that use accelerometer(s) typically require the user to first position the device in a limited set of orientations. For example, the user has to secure the device on their body such that a dedicated axis (i.e. a direction of the device) is substantially and continuously aligned with the direction of the gravitational force throughout the measurement period.

Existing devices are typically unable to detect changes or differentiate signals that correspond to different gaits of the user, resulting in an incorrect count of the steps taken. Motion noises experienced by the devices will also cause false steps to be measured and actual steps to be missed in existing step counting devices.

Also, as the forward and backward swing of a body part to which the device is attached is not same for every step, existing devices are typically unable to correctly identify peaks as a step count due to the inconsistencies in the signal peaks and troughs.

Embodiments of the present invention provide a system and method for activity monitoring that seek to address at least one of the above problems.

SUMMARY

In accordance with a first aspect of the present invention there is provided a device for classifying the activity of a user wearing the device, the device comprising an accelerometer for measuring accelerometer data for a plurality of axes; and a processor configured to:
  identify a most active one of the plurality of axes based on the accelerometer data; and
  classify the activity of the user based on a signal amplitude of the accelerometer data for the most active axis and one or more threshold values.

In accordance with a second aspect of the present invention there is provided a device for counting the number of steps taken by a user wearing the device, the device comprising an accelerometer for measuring accelerometer data for at least one axis; and a processor configured to:
  apply a derivative operator to the accelerometer data in successive processing windows;
  count peaks in the derivative of the accelerometer data in each processing window; and
  eliminate over counted peaks based on time difference between a first peak in a current window and a last peak in a preceding processing window.

In accordance with a third aspect of the present invention there is provided a method for classifying the activity of a user, the method comprising measuring accelerometer data for a plurality of axes; identifying a most active one of the plurality of axes based on the accelerometer data; and classifying the activity of the user based on a signal amplitude of the accelerometer data for the most active axis and one or more threshold values.

In accordance with a fourth aspect of the present invention there is provided a method for counting the number of steps taken by a user, the method comprising measuring accelerometer data for at least one axis; applying a derivative operator to the accelerometer data in successive processing windows; counting peaks in the derivative of the accelerometer data in each processing window; and eliminating over counted peaks based on time difference between a first peak in a current window and a last peak in a preceding processing window.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
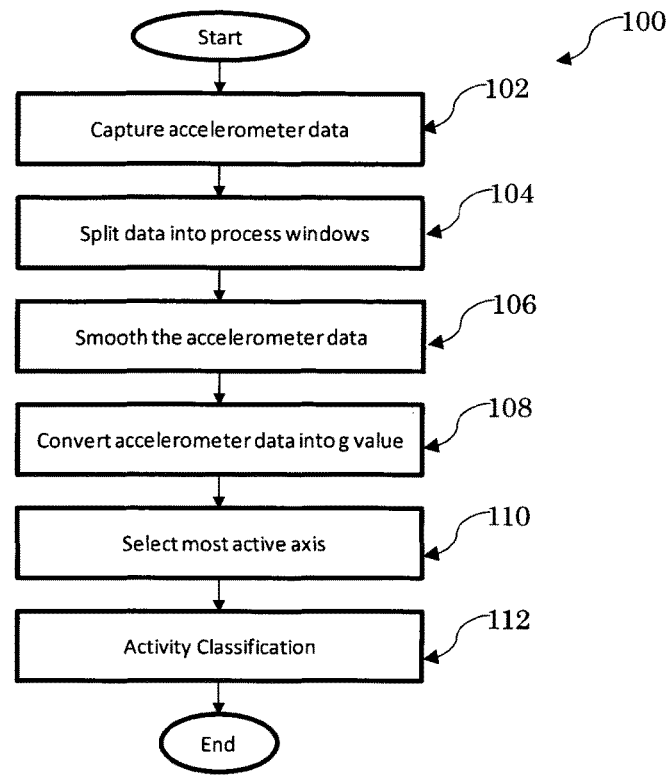
FIG. 1—Shows the process of activity classification according to an example embodiment.

Embodiments of the present invention relate to a wearable device and method for classifying the activity of the user and a wearable device and method of counting the number of steps taken by the user. In one non-limiting example embodiment, the device is worn on the wrist of the user and is configured to obtain the user's acceleration information for processing to classify the activity of the user and/or to count the number of steps taken by the user.

The present specification also discloses an apparatus, which may be internal and/or external to the wearable device in example embodiments, for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below. In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

FIG. 1 shows a flowchart 100 illustrating a method for classifying the activity of a user according to an example embodiment, the method comprising:

At step 102, obtaining the acceleration signals of a user through the wearable device, at step 104, splitting the acceleration signals data into a plurality of processing windows;

and in each processing window, at step 106, smoothing the data with a moving average function, at step 108, the accelerometer data is converted into g value data, at step 110, identifying the most active axis of the acceleration signals, at step 112, classifying the activity of the user based on the acceleration signals from the most active axis, Details of example features that may be used separately and/or in combination with one or more of the other example features will be described next.

Processing Windows

The size of a window is herein described as the time duration of the window, by way of example only. It was found that accuracy suitable for classifying activities and/or counting of steps can for example, but without limitation, be achieved by utilizing window sizes between about >0 to 5 seconds depending on specific accuracy requirement. Generally, a longer window size can lower the chance of an over-counted peak in a window transition area and may thus increase the accuracy. A shorter window may better capture the transition between different activities, which can happen within a very short period of time.

Smoothing of Accelerometer Data

Figure 2:
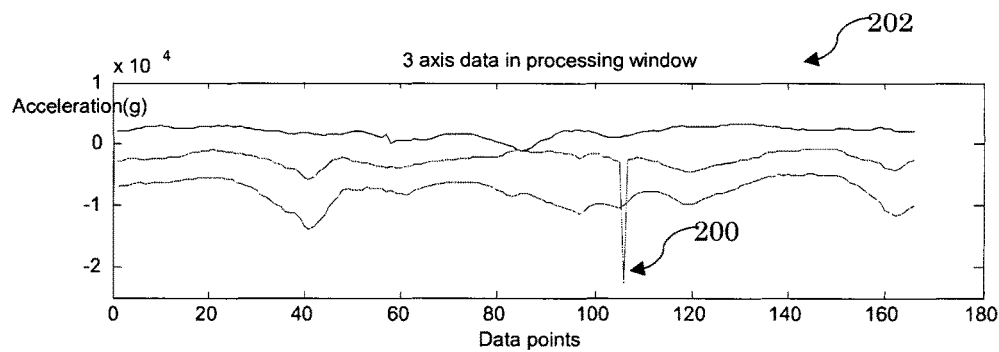
FIG. 2—Shows a spike in the raw accelerometer data.

Raw accelerometer data are typically noisy. A stray spike 200 in example accelerometer data 202 is shown in FIG. 2. The stray spike 200 may result in the wrong axis being identified as the most active axis for the subsequent processing. In example embodiments, smoothing is advantageously applied to the raw accelerometer data 202. Preferably, smoothing is achieved by applying a moving average operation to the raw accelerometer data 200.

Figure 3:
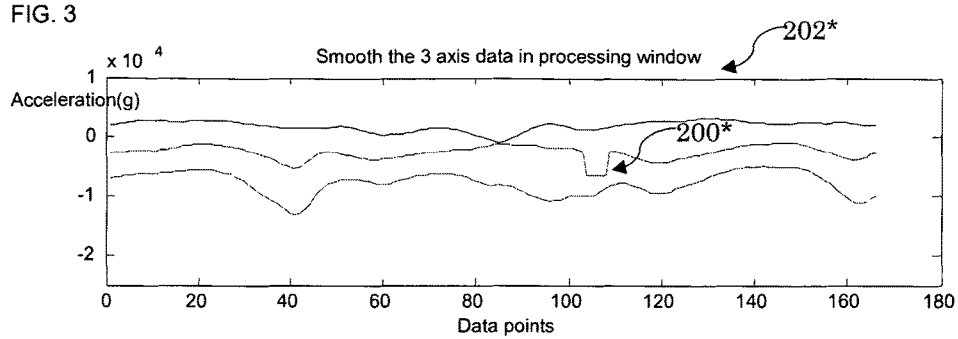
FIG. 3—Shows the accelerometer data of FIG. 2 with the attenuated spike after applying a smoothing process according to an example embodiment.

FIG. 3 shows the accelerometer data 202* after smoothing according to one example embodiment, with an attenuated spike 200* that preferably does not affect the identification of the most active axis for the subsequent processing.

Most Active Axis

The most active axis in example embodiments is identified as the accelerometer axis with the greatest amplitude signal, representative of the contributory effect of the gravitational force and the impact force of the wearer's foot on the ground. In other word, the most active axis in example embodiments the accelerometer axis that is closest to the vertical direction, i.e. substantially perpendicular to the earth.

Advantageously, the most active axis can be easily identified over the other axes regardless of the position or orientation in which the device is being used or worn by the user.

The most active axis in a preferred embodiment is selected by comparing the smoothed x, y and z-axis (i.e. the three accelerometer axes irrespective of actual orientation relative to the ground) data in each window, referred to herein as the moving average. The absolute value of each axis from each window is determined, referred to herein as the absolute moving average. The mean value of each axis based on the absolute value is then determined, referred to herein as the mean absolute moving average. From a comparison of the three mean values, the axis with the largest mean value is identified as the most active axis for each window, in a preferred embodiment.

Activity Classification

The user's activity is classified into light activity, moderate activity or heavy activity state using the moving average data from the most active axis in example embodiments.

Figure 4:
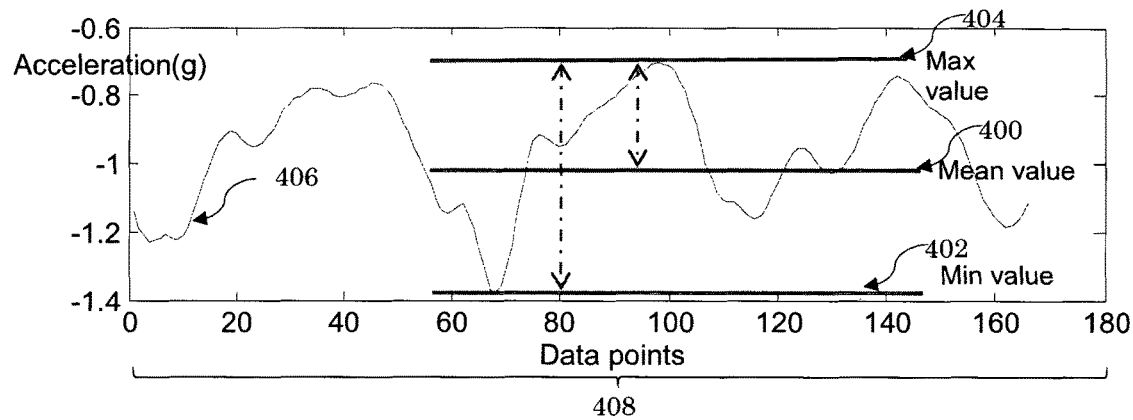
FIG. 4—Shows example signal amplitudes and determined characteristics of an accelerometer signal according to an example embodiment.

In one embodiment, the signal amplitude of the most active axis is calculated by subtracting the mean 400 or minimum (min) g-value 402 from the maximum (max) g-value 404 of most active axis data 406 in, for example, a window 408 with a size between about >0 to 5 s, as shown in FIG. 4.

Figure 5:
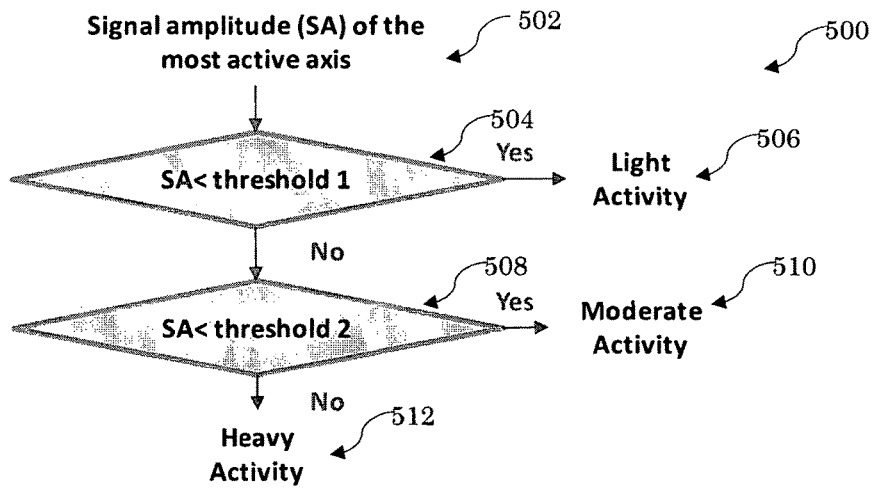
FIG. 5—Shows the process of classifying activity using threshold levels according to an example embodiment.

FIG. 5 shows a flowchart 500 illustrating the process of classifying activity using threshold levels, according to an example embodiment. In the example case that the device is wrist-worn by the user, experimental results (see FIG. 6) has shown that, for example, the threshold levels of 0.1 g and 1 g can be used for activity classification.

At step 502, the signal amplitude (SA) of the most active axis is determined. In step 504, if SA is smaller than a threshold 1, for example SA<0.1 g, classification into the light activity state is performed, see step 506. In step 508, if SA is smaller than a threshold 2, for example SA<1 g, classification into the moderate activity state is performed, see step 510. In other words, in one example for 0.1 g≤SA≤1 g, the classification is into the moderate activity state. If SA the threshold 2, for example SA≥1 g, classification into the heavy activity state is performed, see step 512.

Examples for the Classifications Include:

Light activity—Stationary motions such as standing still, waiting for traffic lights to turn green or typing (e.g. on desk), Moderate activity—Slow walking, brisk walk Heavy activity—Jogging, running Most other activities e.g. climbing stairs, cycling, swimming, playing football, which involve the movement of the body can also be classifiable in example embodiment, e.g. based on:

Further splitting into multiple SA thresholds (on top of the thresholds 1 & 2 in the example above) that corresponds to each of the different activities and/or Further processing of the above 3 generic classifications can be performed in example embodiments by:

Filtering and identification using frequency classifications and/or signal matching techniques.

Figure 6:
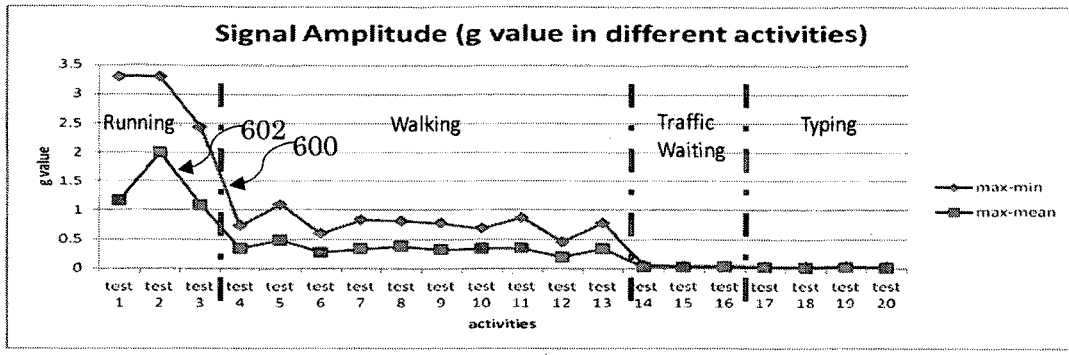
FIG. 6—Shows the signal amplitude measured during different activities according to an example embodiment.
Figure 7:
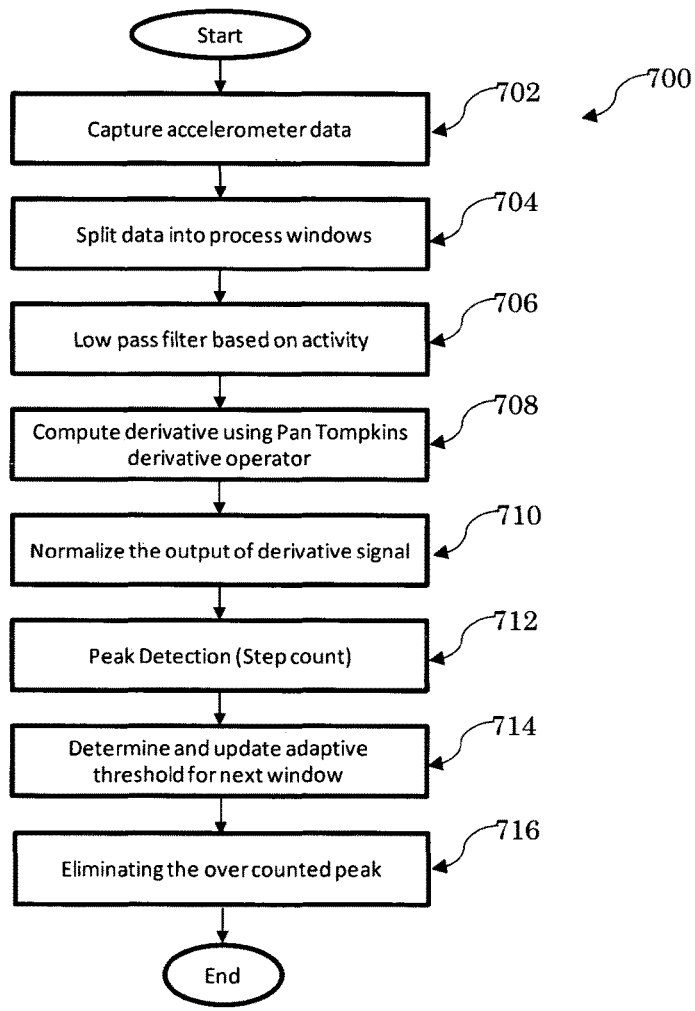
FIG. 7—Shows the process of peak detection and step count according to an example embodiment.

With reference to FIG. 6, plots 600 and 602 show the SA for the most active axis calculated based on the maximum value minus the minimum value in the processing window, and calculated based on the maximum value minus the mean value in the processing window, respectively. As can be seen from FIG. 6, basing the SA on the maximum value minus the mean value in the processing window can be preferred for classification based on thresholds, as it results in a smoother plot with reduced absolute values and narrower bands of values in the respective activity regions, FIG. 7 shows a flow chart 700 illustrating a process for counting steps according to an example embodiment. At step 702, the accelerometer data is captured. At step 704, the data is split into process windows. At step 706, low pass filtering is applied to the data from the most active axis based on classified activity. At step 708, a derivative of the filtered data using Pan Tompkins derivative operator is computed. At step 710, the output of the derivative signal is normalized. At step 712, peak detection is performed for step counting.

At step 714, an adaptive threshold value is determined based on the current process window and updated to be used for the next process window. At step 716, over counted peaks are eliminated.

Details of example features that may be used separately and/or in combination with one or more of the other example features will be described next.

Low Pass Filter Based on Activity Type (Step 706, FIG. 7)

The cut-off frequency of the low pass filter is preferably adjusted based on the activity type to remove the correct frequency range of motion noise. Choosing a correct cut-off frequency can advantageously improve the signal geometry for avoiding false peaks or undetected peaks during the subsequent peak detection processing.

In example embodiments, the activity type may be input by the user, or may be identified using the activity classification method and device described above, or by any other method or device.

Pan Tompkins Derivative Operator (Step 708, FIG. 7)

$$y(n)=(\tfrac{1}{8})[2x(n)+x(n-1)-x(n-3)-2x(n-4)] \quad \text{Equation (1).}$$

where n denotes the data point, and n>4

Pan Tompkins Derivative operator in equation (1) is used in a preferred embodiment to further improve the accuracy of peak detection by advantageously enlarging the slope information and optimizing the signal condition for peak detection.

During normal walking and running, for example arm swings are usually in sync with the opposite leg. For example, the right arm swings forward when the left feet steps forward and vice versa. Based on this reason, one acceleration peak is detected in e.g. a wrist-worn device for every step taken by the user.

Figure 8:
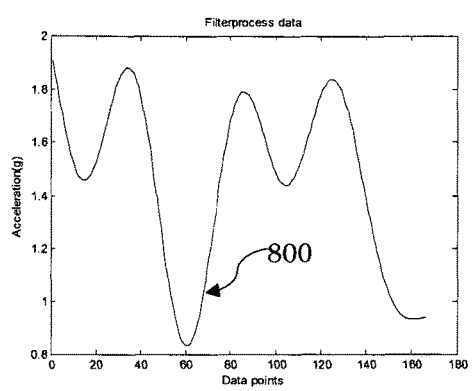
FIG. 8—Shows the signal waveform of a wrist-worn device before and after applying the Pan Tompkins derivation operator according to an example embodiment.
Figure 8:
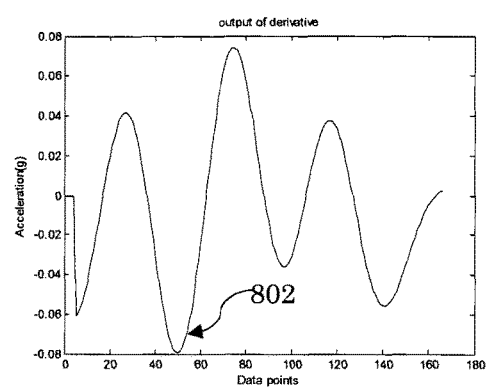

Acceleration changes can also depend on the change in hand swing and impact force of feet. During normal walking condition, the impact force is typically not strong enough and most of the acceleration changes in e.g. a wrist-worn device are due to the hand swing. As the forward and backward swing of the hand is typically not the same for each step, the inconsistent peaks and troughs of the signal waveform can make it difficult to implement an accurate peak detection algorithm, and in a preferred embodiment, the Pan Tompkins derivation operator results in a more consistent peaks and troughs pattern. FIGS. 8a) and b) show the signal waveform of a wrist-worn device before (curve 800) and after (curve 802) applying Pan Tompkins derivation operator according to an example embodiment, respectively.

Normalization (Step 710, FIG. 7)

The normalization process in example embodiments is preferred such that the derivative signals are scaled correctly for the peak detection processing. In one embodiment, the signal is normalized by first subtracting the minimum value of the signal from the signal and then dividing by the maximum value of the subtracted signal.

Peak Detection (Step 712, FIG. 7)

A peak will be detected (i.e. a step counted), when the normalized derivative signal exceeds a threshold level, according to example embodiments. As the data is now normalized (for example min value=0, max value=1), a threshold value $\Delta_1$ for a first processing window can e.g. be set to any pre-determined value between >0 and 0.5.

Determining and Updating Adaptive Threshold (Step 714, FIG. 7)

Figure 9:
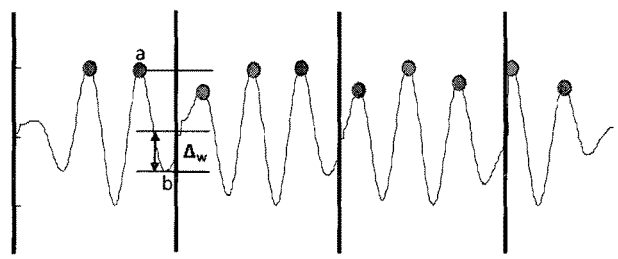
FIG. 9—Shows the adaptive threshold value ($\Delta_w$) used for processing of subsequent window(s) according to an example embodiment.

As shown in FIG. 9, an adaptive threshold value ($\Delta_w$) will be determined and used for subsequent windows, which can be set at any pre-determined value between about >0% and 50% of the difference between the last peak and valley values of the current window. In one example:

$$\Delta_w = (a-b) * 0.5 \qquad \text{Equation (2):}$$

where $\Delta_w$=adaptive threshold value of a next window w, a=last peak value in a current window (w−1), and b=last valley value in the said current window (w−1), and w≥2.

Elimination of Over Counted Peaks (Step 716, FIG. 7)

It was found by the inventors that the Pan Tompkins derivative operation can have a tendency to generate a false first peak in the subsequent windows which can result in over counting of peaks, i.e. steps.

Figure 10:
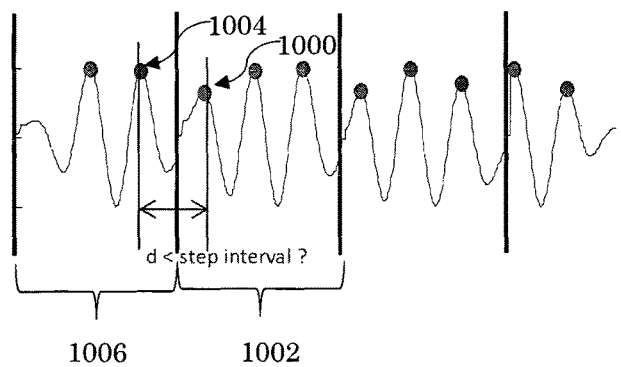
FIG. 10—Shows peak to peak distance between the peaks for two consecutive windows according to an example embodiment.

FIG. 10 illustrates the method of advantageously identifying such false peaks to be removed from the count in a preferred embodiment. The false peaks are identified by checking the distance d between a first peak 1000 of the current measured window 1002 and the last peak 1004 of the previous window 1006.

A threshold may be set at 4 steps per second in one embodiment. For example, in the data point domain of a sampling rate of 80 Hz, the distance threshold may be set at 20 data points based on 4 steps per second. If the peak to peak distance d is smaller than 20 data points, the current peak 1200 is identified as false and is removed from the step count.

Figure 11:
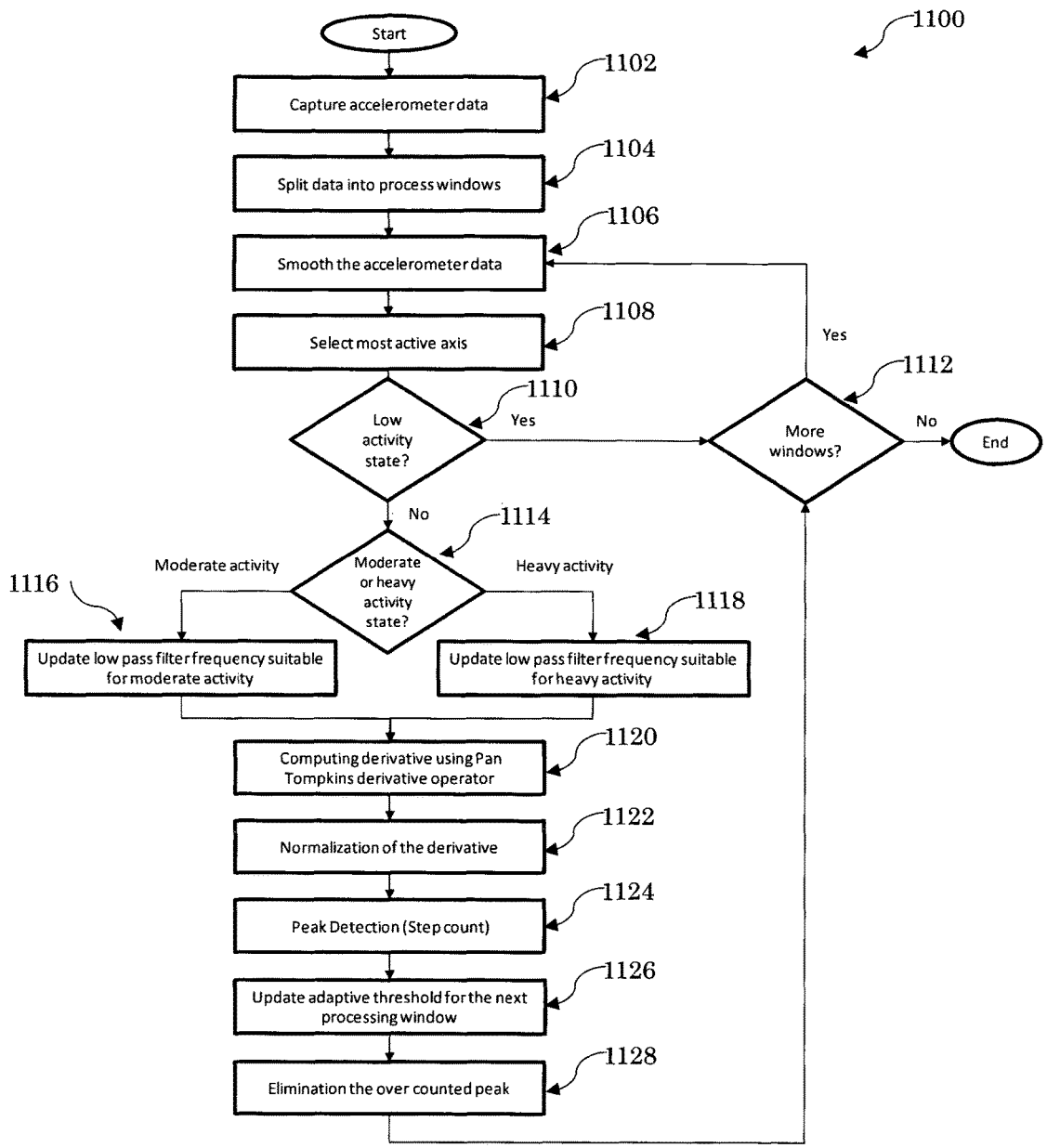
FIG. 11—Shows the process flow of activity classification and step count are being performed according to an example embodiment.

FIG. 11 shows a flow chart illustrating the process flow 1100 of one embodiment, in which both the activity classification and the activity based step counting techniques are integrated into a single wrist wearable device.

At step 1102, acceleration data of the user is captured by the device through a 3-axis accelerometer. At step 1104, the accelerometer signal is split into processing windows between about >0 to 5 seconds. At step 1106, the signal in each window is smoothed by performing a moving average function. At step 1108, the most active axis is identified by comparing the mean absolute moving average value of each axis. The axis with the largest value will be the most active axis.

At steps 1110 and 1114, the activity in each window is classified by calculating the signal amplitude (max-mean) of the moving average signal of the most active axis. Classification will be based on 0.1 g and 1 g thresholds in one non-limiting example. Once a low activity state is identified (step 1110), the process will move on to the next window (step 1112), as no steps are required to be counted.

For moderate and heavy activity states (step 1114), the step counting is performed. At step 1116 and 1118, the cut-off frequency of the low pass filter for each window will be updated based on the activity identified, and the low pass filtering applied accordingly.

At step 1120, the Pan Tompkins derivative operator is then applied. At step 1122, the derivative signal is then normalized to adjust the signal amplitude within, for example, 0 to 1 in each window (first subtracting the minimum value of the signal from the signal and then dividing by the maximum value of the subtracted signal in one non-limiting example).

At step 1124, peak detection is then performed where each peak detected contributes to a step count. In the first window after transiting to a moderate or heavy activity state from a light activity state, the threshold will be set between >0 to 0.5 in one non-limiting example. In other words, a first window transiting from a light activity state does not typically require step elimination. For subsequent windows (be it being a moderate or heavy activity state), over counted peak detection and elimination is advantageously performed until a light activity state is detected for the window. In the subsequent windows, an adaptive threshold is used and will be set between about >0 to 50% of the height difference between the last peak and valley of the previous window, in one non-limiting example, step 1126.

At step 1128, false peaks originating from the Pan Tompkins operation are then removed using e.g. a peak to peak distance (current window first peak vs. previous window last peak) threshold. The threshold in one non-limiting example is based on 4 steps per second. For example, in the data point domain of a sampling rate of 80 Hz, the distance threshold is set at 20 data point. If the peak to peak distance is smaller than 20 data points, the current peak is identified as false and is removed from the step count.

The process for the next window will loop back and follow through steps 1106 to 1128 described above.

Figure 12:
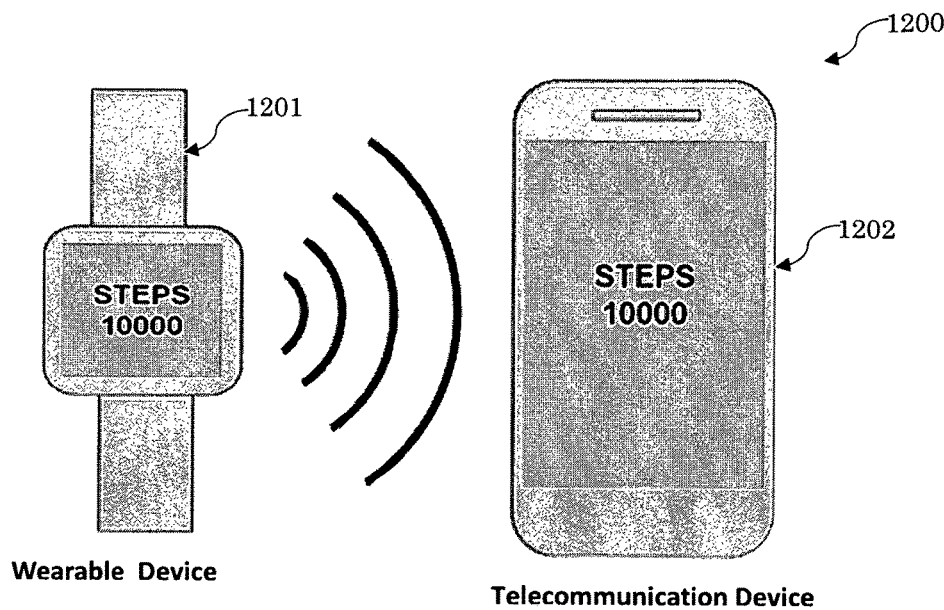
FIG. 12—Shows schematic drawing of an assembly comprising a wearable device and a communication device, according to an example embodiment.

FIG. 12 shows an assembly 1200 comprising a wearable device in the form of a wrist watch 1201 according to an example embodiment. It will be appreciated that in different embodiments the device may also be in any other form suitable to be worn on any part of the user's body such as his/her arms, waist, hip or foot. The wrist watch 1201 classifies the user's activity and/or computes the number of steps taken by the user and communicates the result(s) wirelessly to a telecommunication device of the assembly 1200 such as a mobile phone 1202 or other portable electronic devices, or computing devices such as desk top computers, laptop computer, tab computers etc.

Figure 13:
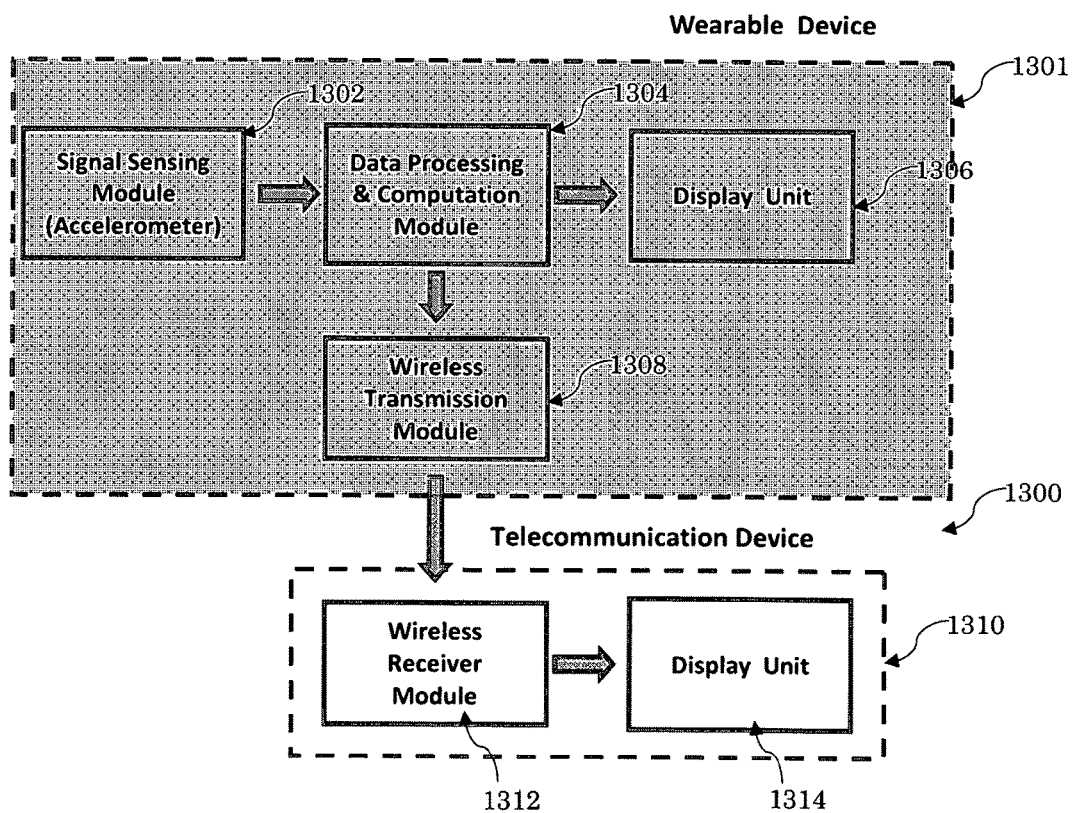
FIG. 13—Shows a block diagram of an assembly comprising a wearable device and a communication device, according to an example embodiment.

FIG. 13 shows a schematic block diagram of an assembly 1300 comprising a wearable device 1301 according to an example embodiment, for classifying activity and/or counting steps of the user. The device 1301 includes a signal sensing module 1302, such as an accelerometer or gyroscope, for obtaining the acceleration information of the user.

One non-limiting example of a preferred accelerometer that can be adapted for use in the device is a triple-axis accelerometer MMA8652FC available from Freescale Semiconductor, Inc. This accelerometer can provide the advantage of measuring acceleration in all three directions with a single package. Alternatively, several single-axis accelerometers oriented to provide three-axis sensing can be used in different embodiments.

The device 1301 also includes a data processing and computational module 1304, such as a processor, which is arranged to receive and process the acceleration information from the signal sensing module 1302. The device 1301 also includes a display unit 1306 for displaying a result to a user of the device 1301. The device 1301 in this embodiment further includes a wireless transmission module 1308 arranged to communicate wirelessly with a telecommunications device 1310 of the assembly 1300. The telecommunication device 1310 includes a wireless receiver module 1312 for receiving signals from the wearable device 1301 and a display unit 1314 for displaying a result to a user of the telecommunication device 1310.

Figure 14:
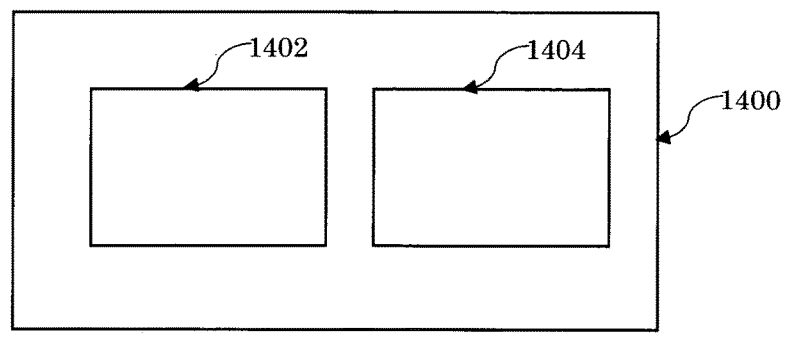
FIG. 14—Shows a block diagram of a device for classifying the activity of a user according to an example embodiment.

FIG. 14 shows a block diagram of a device 1400 for classifying the activity of a user wearing the device, according to one embodiment. The device 1400 comprises an accelerometer 1402 for measuring accelerometer data for a plurality of axes; and a processor 1404 configured to identify a most active one of the plurality of axes based on the accelerometer data and to classify the activity of the user based on a signal amplitude of the accelerometer data for the most active axis and one or more threshold values.

The processor 1404 may be configured to apply a smoothing to the accelerometer data prior to identifying the most active axis.

The processor 1404 may be configured to identify the most active axis by determining the axis having the largest mean absolute amplitude of the smoothed signal, which may also be referred to as the largest mean absolute moving average signal value.

The processor 1404 may be configured to classify the activity based on a maximum signal amplitude of the accelerometer data for the most active axis.

The processor 1404 may be configured to classify the activity based on the maximum signal amplitude of the accelerometer data minus the mean signal amplitude for the most active axis.

The processor 1404 may be configured to identify the most active axis and to classify the activity of the user based on accelerometer data measured over a predetermined processing window.

The processing window may be in a range from about >0 to 5 seconds.

Figure 15:
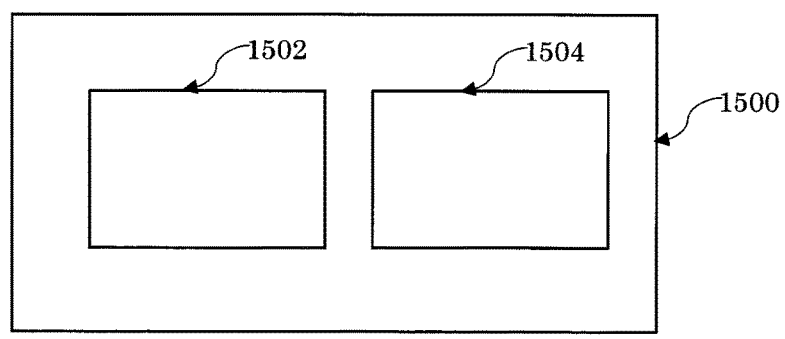
FIG. 15—Shows a block diagram of a device for counting steps of a user according to an example embodiment.

FIG. 15 shows a block diagram of a device 1500 for counting the number of steps taken by a user wearing the device, according to one embodiment. The device 1500 comprises an accelerometer 1502 for measuring accelerometer data for at least one axis; and a processor 1504 configured to apply a derivative operator to the accelerometer data in successive processing windows, to count peaks in the derivative of the accelerometer data in each processing window, and to eliminate over counted peaks based on time difference between a first peak in a current window and a last peak in a preceding processing window.

The processor 1504 may be configured to count the peaks based on a first threshold value if the current processing window is a first processing window after transiting from a light activity state to a moderate or a heavy activity state.

The processor may further be configured to update an adaptive threshold for the next window. The adaptive threshold for the next window may be based on the difference in signal amplitude for a last successive peak and valley pair in the current processing window. The adaptive threshold for the next window may be between about >0 to 50% of the difference in signal amplitude for the last successive peak and valley pair in the current processing window.

The processor 1504 may be configured to eliminate peaks from the peak count in the current window if the time difference between the first peak in the current window and the last peak in the preceding processing window is smaller than a second threshold value. The second threshold value may be about ¼ seconds. The derivative operator may comprise a Pan Tomkins derivative operator.

The devices 1400, 1500 may be implemented in a wearable device.

The devices 1400, 1500 may be implemented in an assembly comprising a wearable device and a communication device.

The devices 1400, 1500 may be implemented in an assembly comprising a wearable device and a wireless communication device.

Figure 16:
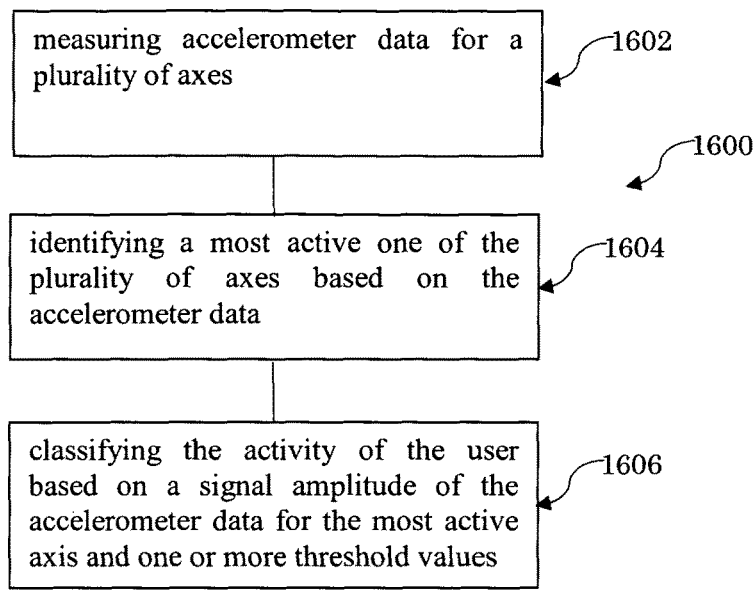
FIG. 16—Shows a flow chart illustrating a method for classifying the activity of a user according to an example embodiment.

FIG. 16 shows a flow chart 1600 illustrating a method for classifying the activity of a user, according to an example embodiment. At step 1602, accelerometer data is measured for a plurality of axes. At step 1604, a most active one of the plurality of axes is identified based on the accelerometer data. At step 1606, the activity of the user is classified based on a signal amplitude of the accelerometer data for the most active axis and one or more threshold values.

The method may comprise applying a smoothing to the accelerometer data prior to identifying the most active axis.

The method may comprise identifying the most active axis by determining the axis having the largest mean absolute value of the smoothed signal, which may also be referred to as the largest mean absolute moving average signal value. The method may comprise classifying the activity based on a maximum signal amplitude of the accelerometer data for the most active axis.

The method may comprise classifying the activity based on the maximum signal amplitude of the accelerometer data minus the mean signal amplitude for the most active axis.

The method may comprise identifying the most active axis and classifying the activity of the user based on accelerometer data measured over a predetermined processing window.

The processing window may be in a range from about >0 to 5 seconds.

Figure 17:
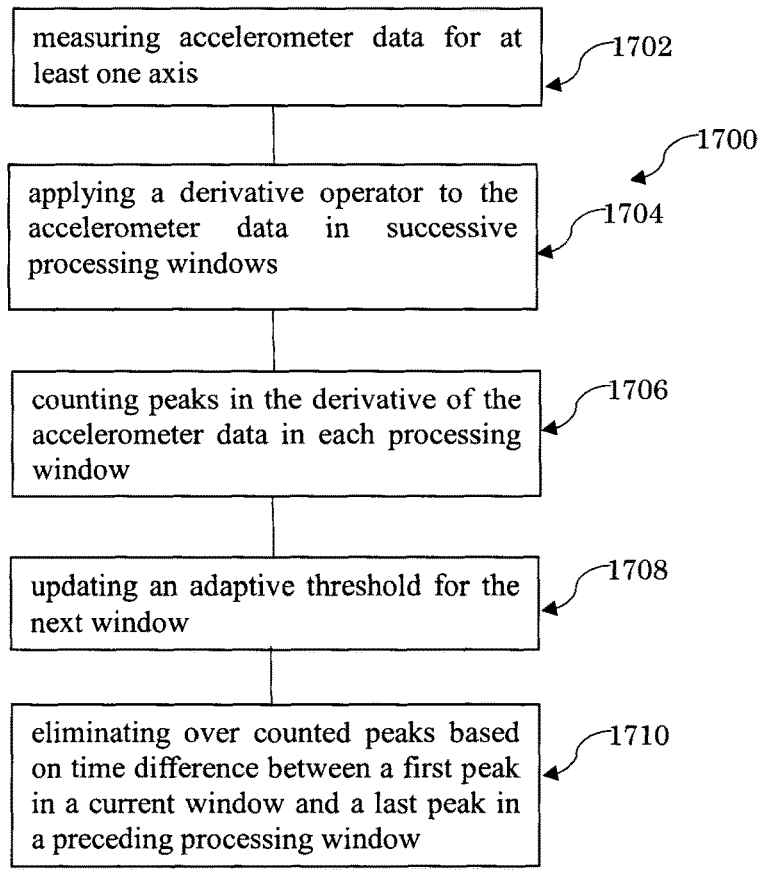
FIG. 17—Shows a flow chart illustrating a method for counting steps of a user according to an example embodiment.

FIG. 17 shows a flow chart 1700 illustrating a method for counting the number of steps taken by a user. At step 1702, accelerometer data is measured for at least one axis. At step 1704, a derivative operator is applied to the accelerometer data in successive processing windows. At step 1706, peaks in the derivative of the accelerometer data in each processing window are counted. At step 1708, over counted peaks are eliminated based on time difference between a first peak in a current window and a last peak in a preceding processing window.

The method may comprise counting the peaks based on a first threshold if the current processing window is a first processing window after transiting from a light activity state to a moderate or a heavy activity state.

The method may further comprise updating an adaptive threshold for the next window. The adaptive threshold for the next window may be based on the difference in signal amplitude for a last successive peak and valley pair in the current processing window. The adaptive threshold for the next window may be between about >0 to 50% of the difference in signal amplitude for the last successive peak and valley pair in the current processing window.

The method may comprise eliminating peaks from the peak count in the current processing window if the time difference between the first peak in the current processing window and the last peak in the preceding processing window is smaller than a second threshold value. The second threshold value may be about ¼ seconds.

The derivative operator may comprise a Pan Tomkins derivative operator.

Example embodiments of the present invention advantageously do not require the device to be attached at a fixed orientation throughout the monitoring period. This is because the device in example embodiments constantly detects within processing windows for the most active axis (which will be the one closest to the direction of the impact force), to be used for subsequent processes. The most active axis can be identified in example embodiments by looking for the axis having the largest mean absolute moving average acceleration signal within each window.

Embodiments of the present invention can advantageously be able to detect changes and differentiate the signals corresponding to light, moderate or heavy states by splitting the accelerometer data into process windows and observing the signal amplitude (e.g. max-mean or max-min) against threshold levels (e.g. 0.1 g and 1 g) within each window.

In embodiments of the present invention, motion noise can advantageously be correctly removed using low pass filters with suitable cut-off frequencies depending on the activity.

In embodiments of the present invention, a Pan Tompkins derivative operation together with a peak elimination algorithm based on peak distance and adaptive thresholds based on max-min value of a peak advantageously helps the device and method to accurately identify peaks as step counts.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. Also, the invention includes any combination of features, in particular any combination of features in the patent claims, even if the feature or combination of features is not explicitly specified in the patent claims or the present embodiments.

For example, while a wrist-worn device is described in some embodiments, the device may be worn on the arms, hip, waist or foot of the user. Also, the device and method may perform only one of the activity classification and the step counting as described above, or both at the same time.

The invention claimed is:

1. A device for classifying the activity of a user wearing the device, the device comprising:
   an accelerometer for measuring accelerometer data for a plurality of axes; and
   a processor configured to:
      identify a most active one of the plurality of axes based on the accelerometer data; and
      classify the activity of the user into different non-stationary activities based on a signal amplitude of the accelerometer data for the most active axis and respective different threshold values for the different non-stationary activities.

2. The device as claimed in claim 1, wherein the processor is configured to apply a smoothing to the accelerometer data prior to identifying the most active axis.

3. The device as claimed in claim 2, wherein the processor is configured to identify the most active axis by determining the axis having the largest mean absolute amplitude of the smoothed signal.

4. The device as claimed in claim 1, wherein the processor is configured to classify the activity based on a maximum signal amplitude of the accelerometer data for the most active axis.

5. The device as claimed in claim 1, wherein the processor is configured to identify the most active axis and to classify the activity of the user based on accelerometer data measured over a predetermined processing window.

6. A method for classifying the activity of a user, the method comprising:
   measuring accelerometer data for a plurality of axes;
   identifying a most active one of the plurality of axes based on the accelerometer data; and
   classifying the activity of the user into different non-stationary activities based on a signal amplitude of the accelerometer data for the most active axis and respective different threshold values for the different non-stationary activities.

7. The method as claimed in claim 6, comprising applying a smoothing to the accelerometer data prior to identifying the most active axis.

8. The method as claimed in claim 7, comprising identifying the most active axis by determining the axis having the largest mean absolute value of the smoothed signal.

9. The method as claimed in claim 6, comprising classifying the activity based on a maximum absolute signal amplitude of the accelerometer data for the most active axis.

10. The method as claimed in claim 6, comprising identifying the most active axis and classifying the activity of the user based on accelerometer data measured over a predetermined processing window.

* * * * *